United States Patent [19]

Diamond et al.

[11] 3,931,269

[45] Jan. 6, 1976

[54] ALPHA-ACYL SUBSTITUTED NAPHTHYLACETIC ACIDS

[75] Inventors: Julius Diamond, Lafayette Hill; Ching Tan Tsuei, Lansdale, both of Pa.

[73] Assignee: William H. Rorer, Inc., Fort Washington, Pa.

[22] Filed: Feb. 28, 1975

[21] Appl. No.: 553,961

Related U.S. Application Data

[62] Division of Ser. No. 422,479, Dec. 6, 1973, Pat. No. 3,892,803.

[52] U.S. Cl............................................. 260/455 R
[51] Int. Cl.². ...................................... C07C 153/07

[58] Field of Search .................................. 260/455 R

[56] References Cited
UNITED STATES PATENTS 3,829,467   8/1974   Diamond et al. ............... 260/455 R Primary Examiner—Lewis Gotts
Assistant Examiner—Phillips D. R.
Attorney, Agent, or Firm—James A. Nicholson

[57] ABSTRACT

Novel naphthylalkanoic acids and their derivatives are described. Therapeutic compositions and method of treatment of inflammation is also disclosed.

5 Claims, No Drawings

ALPHA-ACYL SUBSTITUTED NAPHTHYLACETIC ACIDS

CROSS REFERENCES TO RELATED APPLICATIONS

This is a division of application Ser. No. 422,479, filed Dec. 6, 1973, now U.S. Pat. No. 3,892,803.

SUMMARY OF THE INVENTION

This invention describes novel hydroxy, halo and thionaphthylalkanoic acids and their derivatives and their use in therapeutic compositions. In addition, this invention describes the preparation of these hydroxy, halo and thionaphthylalkanoic acids and their derivatives. When the compounds of this invention are administered to mammals, they afford significant treatment for the relief of inflammation and associated pain and fever.

They further provide analgesic and antipyretic methods for the relief and treatment of pain and fever.

BACKGROUND OF THE INVENTION

Continued studies have been carried out in research to develop drugs which would significantly inhibit the development of inflammation and relieve the pain and fever associated with it. Much of this effort has been carried out in the steroid field; however, there have been compounds developed which are non-steroidal and have included such as the alkanoic acids derived from the biphenyl ring system.

We have unexpectedly found that when a hydroxy, halo, or thio group or derivative thereof is present in the α-position of the side chain of a 6-methoxy-2-naphthylacetic acid molecule, pharmacological properties exist in the molecule which are useful for the relief and inhibition of inflammation conditions.

We have also found that the compounds of this invention are effective in the treatment of inflammation and the control of arthritic conditions associated with inflammation.

We have further found that α-hydroxy, halo and thio-2-naphthylacetic acids and their derivatives are novel.

We have also found that the compounds of this invention possess useful analgesic and antipyretic properties and are useful in the treatment of pain and fever.

We have still further found an entirely new class of antiinflammatory, analgesic and antipyretic pharmaceutical compositions which contain an α-hydroxy, halo or thio-2-naphthylacetic acid or derivative thereof as active ingredient.

We have also found a convenient method for synthesizing these compounds.

DESCRIPTION AND PREFERRED EMBODIMENTS

This invention comprises a class of novel chemical compounds which are 6-methoxy-2-naphthylacetic acids or derivatives to which is attached a hydroxy, hydroxy derivative, halo, mercapto, or thio derivative at the α-position of the acetic acid side chain. Also the naphthyl ring may further be substituted.

This invention also describes a new method for treating inflammation as well as pain and fever and also novel therapeutic compositions.

The compounds of this invention can be represented by the generic structure which is described by general formula I

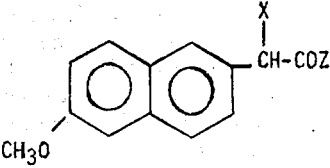

I where X is:
halo,
hydroxy,
loweralkoxy,
loweracyloxy,
aroyloxy,
carbloweralkoxy,
carbamyloxy,
loweralkylcarbamyloxy,
diloweralkylcarbamyloxy,
loweralkanesulfonyloxy,
benzenesulfonyloxy,
toluenesulfonyloxy,
carboxyacyloxy,
carboxyaroyloxy,
mercapto,
loweralkylthio,
acylthio,
aroylthio,
sulfo,
sulfino,
loweralkylsulfinyl,
loweralkylsulfonyl,
thioacylthio,
thiosulfo,
thiocyanato,
amidinothio,
carbamylthio,
loweralkylcarbamylthio,
diloweralkylcarbamylthio,
loweralkoxythiocarbonylthio,
loweralkoxycarbonylthio,
diloweralkylthiocarbonylthio,
arloweralkoxycarbonylthio,
carboxyaroylthio or
carboxyacylthio;
Z is hydrogen,
—OH,
loweralkoxy,
arloweralkoxy,
—NH$_2$,
loweralkylamino,
diloweralkylamino,
cycloloweralkylamino,
=NA (where A is loweralkylidenyl or heteroloweralkylidenyl),
=NOH,
=NHNH$_2$ or
—OM (where M is an alkali, alkaline earth or aluminum metal or an ammonium salt).

The preferred compounds of this invention are described by formula I where Z is =OH, amino, diloweralkylamino and =OM.

The more preferred compounds are described where X is halo, hydroxy, loweracyloxy, loweralkanesulfonyloxy, benzenesulfonyloxy, toluenesulfonyloxy, mercapto or acylthio.

The most preferred compounds are described where X is chloro or hydroxy.

The compounds of this invention contain an asymmetric carbon atom in the acid side chain. As a result, the above compounds of formula I may be obtained as racemic mixtures of their dextro (+) and levorotatory (−) isomers. It is to be understood that said d and l isomers as well as the dl mixtures thereof are embraced within the scope of this invention.

The compounds of this invention may be prepared from known starting materials. References to specific starting materials are given where applicable or the following methods of synthesis may be used where appropriate.

Condensation of 2-methoxynaphthalene with a loweralkyl (preferably t-butyl) or aralkyl oxalyl chloride in the presence of anhydrous aluminum chloride results in 6-methoxy-2-naphthylglyoxylate. This may then be reduced to the glycolate by catalytic hydrogenation with platinum oxide or under sodium borohydride conditions.

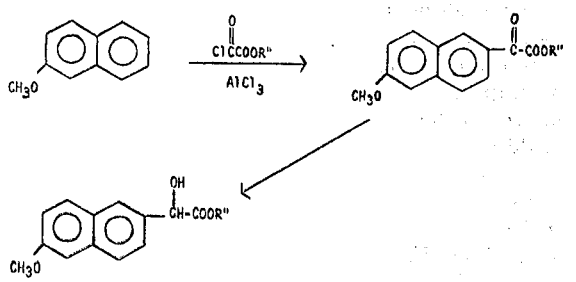

Reaction of 6-methoxy-2-naphthylglycolate ester with a nitrogen base such as ammonia, loweralkylamine, diloweralkylamine, cycloloweralkylamine, a nitrogen containing hetero compound such as piperidine, morpholine, piperazine, hydroxylamine and hydrazine gives the corresponding amide, hydroxamic acid, or hydrazide.

The naphthyl glycolate esters may be hydrolyzed to the corresponding glycolic acids. Reaction of the glycolate ester or glycolic acid with an acyl chloride X'Cl or acyl anhydride X'OX' in the presence of a tertiary amine such as pyridine, picoline, or quinoline results in the formation of an acyloxy compound. Examples of X'Cl and X'OX' include acetyl chloride, acetic anhydride, propionyl chloride, butyryl chloride, succinic anhydride, maleic anhydride, phthalic anhydride, benzoyl chloride, benzoic anhydride, benzyl chlorocarbonate, ethyl chlorocarbonate, dimethylcarbamyl chloride, dibutylcarbamyl chloride, benzenesulfonyl chloride, methanesulfonyl chloride.

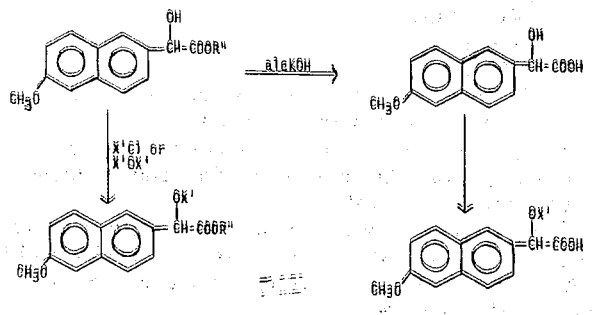

When 6-methoxy-2-naphthyl glycolate is reacted with a phosphorus trihalide, phosphorus pentahalide, phosphorus oxyhalide, sulfurylhalide, thionyl halide, or sulfur halide, the corresponding 6-methoxy-2-naphthyl-α-halo acetate is prepared.

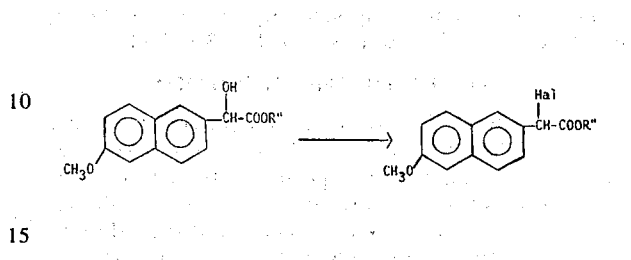

where
R'' is lower alkyl; and
Hal is chloro, bromo or iodo.

Reaction of a naphthyl-α-sulfonate compound with a metal halide (preferably an alkali halide) also results in the corresponding α-halo compound.

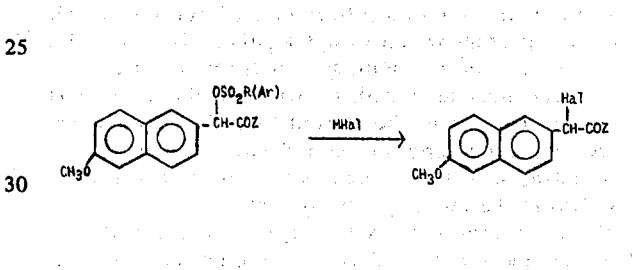

The 6-methoxy-2-naphthyl-α-haloacetic acid may be prepared by heating the ester with acetic acid containing the corresponding hydrogen halide.

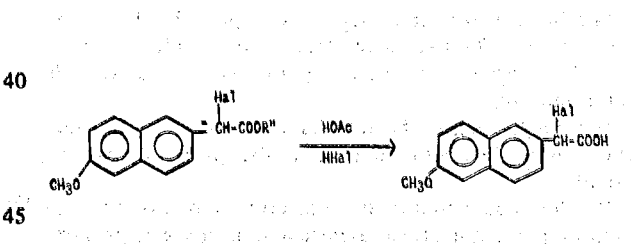

where R'' is lower alkyl.

The substituted naphthyl-α-fluoro compounds may also be obtained from the corresponding α-iodo, α-bromo or α-chloro compounds by reaction with potassium fluoride at about 130°–200°C.

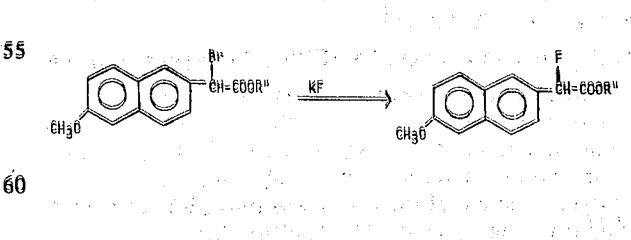

The acid addition salts may be formed by the action of one equivalent of a suitable base with the substituted naphthyl α-haloacetic acid. Suitable bases thus include for example for example the alkali metal alkoxides such as sodium methoxide, etc., and the alkali metal and alkaline earth metal hydroxides, carbonates, bicarbonates, etc. (such as sodium hydroxide, potassium hydroxide, calcium hydroxide, potassium carbonate, sodium bicarbonate, magnesium bicarbonate, etc.). Also, the aluminum salts of the instant products may be obtained by treating the corresponding sodium salt with an appropriate aluminum complex such as aluminum hydroxy chloride hexahydrate, etc. The ammonium salts may be made by reaction with the corresponding amine such as methylamine, diethylamine, β-hydroxyethylamine, piperazine, piperidine, α-methylbenzylamine, cyclohexylamine, triethylamine, phenethylamine, etc.

Reaction of a substituted naphthyl α-halo acetate with a nitrogen base such as ammonia, loweralkylamine, diloweralkylamine, cycloloweralkylamine, a nitrogen containing hetero compound such as piperidine, morpholine, piperazine results in the corresponding amide. The acetate with hydroxylamine gives the corresponding hydroxamic acid, and with hydrazine gives the corresponding hydrazide.

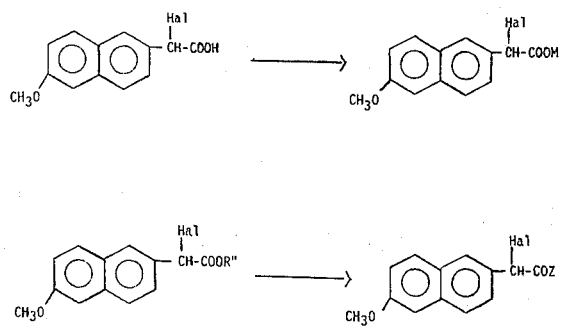

where Z is:
—NH₂,
loweralkylamine,
diloweralkylamino,
cycloloweralkylamino,
—NB (where B is loweralkylidenyl or heteroloweralkylidenyl),
—NHOH or
—NHNH₂.

The naphthyl α-halo acetamides, acethydroxamic acids, and acethydrazides, can be prepared from the corresponding glycolamides with thionyl halides according to the method of I. A. Smith, Chem. Berichte 71B:634 (1938).

The substituted naphthyl α-halo acetic acids and acid derivatives such as their salts, amides or esters may be reacted with various nucleophilic reagents which will replace the α-halogen group. Thus, for example, an alkali hydrosulfide or an alkali thioalkanoate may be reacted to obtain an α-mercapto or α-acylthio compound. Other groups which may also react in this manner include such as an alkali thiobenzoate, alkali loweralkylxanthate, thiourea, alkali thiocyanate, alkali thiosulfate, alkali loweralkylmercaptide, alkali sulfite or an alkali sulfinate. This may also be carried out on the α-sulfonate compounds to obtain the same product.

The naphthyl α-mercapto acetic acids may then be reacted with a loweralkyl chlorocarbonate, an alkali isocyanate in the presence of hydrogen chloride, a loweralkylcarbamyl chloride, a diloweralkylcarbamyl chloride or converted to the metal salt which will react with a carbamyl chloride to form the corresponding α-mercaptoacetic acid derivatives. The α-mercapto acetic acid may also be reacted with succinic anhydride, maleic anhydride or phthalic anhydride to form the corresponding derivative.

The naphthyl α-loweralkylmercapto acetic acid may further be oxidized to the loweralkylsulfinyl and loweralkylsulfonyl groups.

In an analogous manner the various α-mercaptoacetates, α-mercaptoacetamides and α-mercaptoacetic acid salts may be prepared from the corresponding α-haloacetates, α-haloacetamides and α-haloacetic acid salts.

Of course it will be understood by one skilled in the art that variations in the above procedures can be employed which will provide that sequence of reactions which will result in the desired product.

The products of this invention are obtained as racemic mixtures of their dextro and levorotatory isomers since the α-carbon of the side chain is asymmetric. These may be resolved into the dextro and levorotatory optical isomers by conventional methods.

One method of resolution that may be employed is combining the racemic compound with an optically active compound by salt formation, ester formation, or amide formation to form two diastereomeric products. If the instant acids are added to an optically active base, then two diastereomeric salts are produced which possess different properties and different solubilities and can be separated by fractional crystallization. When the salts have been completely separated by repeated crystallization, the base is split off by acid hydrolysis and the pure $d$ or $l$ acids are obtained. Preferably, the acetic acid is reacted in alcoholic or acetone solution with an equivalent amount of the optically active primary, secondary, or tertiary amine such as cinchonidine, cinchonine, quinine, ephedrine, α-methylbenzylamine, sec-butylamine, sec-amylamine, etc. The diastereomeric amine salts produced thereby, are separated by fractional crystallization and each optically active salt is hydrolyzed with dilute mineral acid to produce the dextro or levo form of that acetic acid. Each optical isomer may be reacted then with X′Cl ir XOX′ to produce the corresponding optically active alcoholic derivative. Alternatively, an alkanoate ester may be reacted with an optically active primary or secondary amine such as ephedrine, α-methylbenzylamine, sec-butylamine, etc., to produce a mixture of diastereomeric acetates which may be separated by fraction crystallization. Each optically active amide may be hydrolyzed with mineral acid to its respective optically active acid.

Alternatively, an acetate may be reacted with an optically active alcohol such as $l$-menthol or $d$-borneol, or $l$-α-methylbenzylalcohol, to produce a mixture of diastereomeric acetate esters which may be separated by fractional crystallization. Each optically active ester may be hydrolyzed with mineral acid or alkali to its respective optically active acid. The optically active acids can also be recovered from the α-methylbenzyl esters by hydrogenolysis in the presence of palladium.

In this manner the α-oxy, halo or thio isomers may be prepared.

We have found that the compounds of this invention exercise a useful degree of anti-inflammatory activity in mammals and are effective in the treatment of associated pain and fever and in like conditions which are responsive to treatment with anti-inflammatory agents. In general, the compounds of this invention are indicated for a wide variety of mammalian conditions where the symptoms of inflammation and associated fever and pain are manifested. Exemplary of such conditions are: rheumatic diseases such as rheumatoid arthritis, osteoarthritis and other degenerative joint diseases; soft-tissue rheumatism such as tendinitis; muscular rheumatism such as sciatica; pain and inflammation associated with dental surgery and similar human and veterinary disease conditions exhibiting the foregoing symptoms requiring the use of an anti-inflammatory, analgesic and/or an antipyretic agent.

For these purposes, the compounds of this invention are normally administered orally, topically, parenterally or rectally. Orally, these may be administered in tablets, capsules, suspensions or syrups; the optimum dosage, of course, depending on the particular compound being used and the type and severity of condition being treated. In any specific case the appropriate dosage selected will further depend on factors of the patient which may influence response to the drug; for example, general health, age, weight, etc. Although the optimum quantities of the compounds of this invention to be used in such manner will depend on the compound employed and the particular type of disease condition treated, oral dose levels of preferred compounds when administered to a mammal in dosages of 0.5 to 100 milligrams per kilogram of body weight per day are particularly useful. The preferred range is 0.5 to 15 mg/kg. Comparative dosages may be used in topical, parenteral or rectal administration.

Dosage forms may be prepared according to any method known to the art for the manufacture of pharmaceutical compositions and such compositions may contain one or more agents; for example, sweetening agents, flavoring agents, coloring agents, preserving agents, etc. Further, the active compounds or their derivatives may be administered alone or in admixture with antacids such as sodium bicarbonate, magnesium carbonate, magnesium hydroxide, aluminum hydroxide, magnesium silicate, etc., and non-toxic pharmaceutically acceptable excipients. Such excipients may be, for example, inert diluents such as calcium carbonate, lactose, etc., granulating and disintegrating agents; for example, magnesium stearate, talc, etc., binding agents; for example, starch gelatin, etc., suspending agents; for example, methylcellulose, vegetable oil, etc., dispersing agents; for example, lecithin, etc., thickening agents; for example, beeswax, hard paraffin, etc., emulsifying agents; for example, naturally occurring gums, etc., and non-irritating excipients; for example, cocoa butter and polyethylene glycols.

Various tests in animals can be carried out to show the ability of the 6-methoxy-2-naphthylacetic acids and derivatives of this invention to exhibit reactions that can be correlated with anti-inflammatory activity in humans. One such test is the Carrageenan Paw Edema test, which shows the ability of the instant compounds to inhibit edema induced by injection of an inflammatory agent such as carrageenan into the tissues of the paw of a rat against non-inflammed controls. This carrageenan testing method is known to correlate well with anti-inflammatory activity in humans and is a standard test used to determine anti-inflammatory activity. This correlation can be shown by the activities of compounds known to be clinically active including such as aspirin, phenylbutazone, cortisone, hydrocortisone and prednisolone. In view of the results of this test, the 6-methoxy-2-naphthylacetic acids and derivatives can be considered to be active anti-inflammatory agents.

One method for measuring the pain threshold of the compounds of this invention is the Randall-Selitto test. Analgesic activity is shown by antinociceptive testing of the inflamed foot of rats and a measurement of their pain response.

Antipyretic assay is carried out by yeast-induced fever tests of subcutaneously injected rats. The measurement of rectal temperature is carried out to determine the response by the test compounds.

In view of the results of the above tests, the 6-methoxy-2-naphthylacetic acids and derivatives of this invention are considered to have valuable analgesic and antipyretic properties.

Other tests which can be correlated to show significant activities are the "phenylquinone writhing" test for analgesia, "polyarthritis in rats" and "ultra-violet erythema in guinea pigs."

The following are detailed examples which show the preparation of the compounds of this invention. They are to be construed as illustrations of said compounds and are not intended to be limitations thereof.

EXAMPLE 1

Ethyl 6-methoxy-2-naphthylglyoxylate

Aluminum chloride 52 g. (0.39 mole) is dissolved in dry nitrobenzene (300 ml). 2-Methoxynaphthalene (0.33 mole) is added to the ice-cold solution with mechanical stirring, followed by ethyl oxalyl chloride (0.37) over a 25 minute period. The reaction mixture is kept in an ice-bath for 3 hours and at room temperature for 48 hours. The reaction mixture is poured onto crushed ice (400 g.), is mixed with concentrated hydrochloric acid (150 cc), and water (150 cc) with good stirring. The organic layer is washed twice with water by decantation. Nitrobenzene is removed by steam distillation, the residue collected, dried, and distilled to give ethyl 6-methoxy-2-naphthylglyoxylate.

EXAMPLE 2

Ethyl 6-methoxy-2-naphthylglycolate

Into a Paar hydrogenation bottle is added 0.144 mole of ethyl 6-methoxy-2-naphthylglyoxylate, 2 ml. of 0.1 M - ferrous sulfate solution; 220 ml. of isopropanol, and 1.0 g. of 84.1% platinum oxide. The mixture is shaken for 2 hours at room temperature with hydrogen gas until 0.144 mole of hydrogen is absorbed. The catalyst is then filtered off and the solution is evaporated in vacuo and the residue fractionally distilled to obtain ethyl 6-methoxy-2-naphthylglycolate.

EXAMPLE 3

6-Methoxy-2-naphthylglycolic acid

To a solution of 0.144 moies of ethyl 6-methoxy-2-naphthylglycolate dissolved in 220 ml. of isopropanol is added 38 g. (0.7 mole) of potassium hydroxide. This mixture is then heated at reflux temperature in a nitrogen atmosphere. The solution is concentrated in vacuo to a viscous oil, which is then dissolved in 500 ml. of water and filtered. The filtrate is acidified with 10% HCl and the precipitate is taken up in ether. The ether layer is dried, filtered and the filtrate concentrated to dryness. Recrystallization of residue from benzenecyclohexane 1:1 gives 6-methoxy-2-naphthylglycolic acid.

EXAMPLE 4 l 6-Methoxy-2-naphthylglycolic acid

To a boiling solution of 29.4 g. (0.10 mole) of cinchonidine in 1 liter of absolute ethanol is added a boiling solution of 0.10 mole of dl 6-methoxy-2-naphthylglycolic acid in 500 ml. of absolute ethanol. The solution is stirred briefly then allowed to cool to room temperature overnight. The precipitate is collected and washed with 2 × 25 ml. of ethanol and air dried. Recrystallization from isopropanol gives white needle crystals. This material is hydrolyzed with 200 ml. of 1.2 N-HCl. The white solid is collected, washed with 3 × 50 ml. water and dried at 55°C overnight. Recrystallization from benzenecyclohexane 3:2 gives l 6-methoxy-2-naphthylglycolic acid.

EXAMPLE 5 d 6-Methoxy-2-naphthylglycolic acid

The combined ethanol and isopropanol filtrates from Example 4 are evaporated to dryness. This material is triturated with 1 liter of boiling acetone. The material which does not go into solution is filtered off. The filtrate is evaporated to dryness and hydrolyzed with 100 ml. of 1.2 N-HCl. The precipitate is collected, washed with 3 × 25 ml. of water, and dried at 55°C. Recrystallization from benzenecyclohexane 3:2 gives d 6-methoxy-2-naphthylglycolic acid.

EXAMPLE 6

6-Methoxy-2-naphthylglycolic acid, sodium salt

A solution of 12.4 g. of sodium bicarbonate in 135 ml. of water is added dropwise to a stirred solution of 0.164 moles of 6-methoxy-2-naphthylglycolic acid in 150 ml. of methanol. The solvent is removed in vacuo and the residue is dried by repeated distillations with anhydrous ethanol. The crystalline residue is triturated with ether (100 ml.), collected and washed with ether. The residue is dried in a vacuum desiccator to obtain 6-methoxy-2-naphthylglycolic acid, sodium salt.

When an equimolar amount of sodium bicarbonate in the above reaction is replaced by the compounds of Table I below, then the corresponding salt is prepared.

Table I sodium hydroxide
potassium hydroxide
clacium hydroxide
potassium carbonate
magnesium bicarbonate

EXAMPLE 7

6-Methoxy-2-naphthylglycolic acid, diethylammonium salt

Anhydrous diethylamine (0.11 moles) is added dropwise to a stirred solution of 6-methoxy-2-naphthylglycolic acid (0.10 moles) in 100 ml. of n-hexane at 0°C. The precipitated diethylammonium salt is collected on a filter washed with n-hexane and dried in a vacuum desiccator to obtain 6-methoxy-2-naphthylglycolic acid, diethylammonium salt.

When diethylamine in the above reaction is replaced by an equimolar amount of the compounds of Table I, below, then the corresponding product is prepared.

Table I

| | |
|---|---|
| dimethylamine | α-methylbenzylamine |
| β-hydroxyethylamine | cyclohexylamine |
| piperazine | triethylamine |
| piperidine | phenethylamine |

EXAMPLE 8

N-isopropyl-6-methoxy-2-naphthylglycolamide

Ethyl 6-methoxy-2-naphthylglycolate (0.1 mole) is stirred with 20 ml. of isopropylamine at about 35°C with stirring overnight and the temperature is then raised to reflux for 28 hours. The reaction mixture is evaporated in vacuo and the residue distilled to obtain N-isopropyl-6-methoxy-2-naphthylglycolamide.

When isopropylamine in the above reaction is replaced by an equimolar amount of the compound of the Table I, below, then the corresponding product is prepared.

Table I

| | |
|---|---|
| diethylamine | isothiazolidine |
| ethylmethylamine | piperidine |
| t-butylamine | morpholine |
| cyclopropylamine | N-methylpiperazine |
| N-methylhomopiperazine | |

When isopropylamine in the above reaction is replaced by ammonia, methylamine or dimethylamine and the reaction carried out in a bomb at 150°C, then the product prepared is 6-methoxy-2-naphthylglycolamide, N-methyl-6-methoxy-2-naphthylglycolamide or N,N-dimethyl-6-methoxy-2-naphthylglycolamide.

EXAMPLE 9

Ethyl α-chloro-6-methoxy-2-naphthylacetate

A mixture of 0.747 mole of ethyl α-chloro-6-methoxy-2-naphthylglycolate is stirred with 106.67 g. (0.895 mole) of thionyl chloride at room temperature for 24 hours and then heated to reflux for 6 hours. The cold reaction mixture is poured into 1125 ml. of icecold water with stirring. The mixture is extracted with 800 ml. of ether. The ethereal solution is washed with 450 ml. of cold saturated sodium hydrocarbonate solution followed by washing twice, each time with 250 ml. of cold water. The ethereal solution is dried over anhydrous sodium sulfate and filtered. The solvent is removed in vacuo to obtain ethyl α-chloro-6-methoxy-2-naphthylacetate.

EXAMPLE 10

When the procedure of Example 9 is followed but ethyl 6-methoxy-2-naphthylglycolate is replaced by the dl, d and l glycolates of this invention, then the corresponding dl, d and l α-chloroacetate products are prepared.

EXAMPLE 11

When the procedure of Example 9 is followed but ethyl 6-methoxy-2-naphthylglycolate is replaced by the amides of Example 8, then the corresponding product is obtained.

EXAMPLE 12

α-Chloro-6-methoxy-2-naphthylacetic acid

A mixture of 0.167 moles of the ethyl α-chloro-6-methoxy-2-naphthylacetate and 160 ml. of glacial acetic acid containing 40 ml. of 37% hydrochloric acid is refluxed for 20 hours. The mixture is concentrated under reduced pressure to give a gummy residue. The latter material is dissolved in 300 ml. of n-hexane, washed with ice-cold water (100 ml. total), dried over sodium sulfate and filtered. The hexane is removed to give α-chloro-6-methoxy-2-naphthylacetic acid.

EXAMPLE 13

When the procedure of Example 12 is followed but ethyl α-chloro-6-methoxy-2-naphthylacetate is replaced by the dl, d and l α-chloro-acetates of this invention, then the corresponding dl, d and l α-chloroacetic acids are prepared.

EXAMPLE 14

α-Chloro-6-methoxy-2-naphthylacetic acid, sodium salt

A solution of 12.4 g. of sodium bicarbonate in 135 ml. water is added dropwise to a stirred solution of 0.164 moles of α-chloro-6-methoxy-2-naphthylacetic acid in 150 cc. of methanol. The solvent is removed in vacuo and the residue is dried by repeated distillations with anhydrous ethanol. The crystalline residue is triturated with ether (100 cc.), collected on a filter, and washed with ether. Drying in a vacuum desiccator affords α-chloro-6-methoxy-2-naphthylacetic acid, sodium salt.

When an equimolar amount of sodium bicarbonate in the above reaction is replaced by the compounds of Table I below, then the corresponding salt is prepared.

Table I sodium hydroxide
potassium hydroxide
calcium hydroxide
potassium carbonate
magnesium bicarbonate

EXAMPLE 15

α-Chloro-6-methoxy-2-naphthylacetic acid, diethylammonium salt

Anhydrous diethylamine (0.11 moles) is added dropwise to a stirred solution of α-chloro-6-methoxy-2-naphthylacetic acid (0.10 moles) in 100 ml. of n-hexane at 0°C. The precipitate is collected on a filter, washed with n-hexane, and dried in a vacuum desiccator to obtain α-chloro-6-methoxy-2-naphthylacetic acid, diethylammonium salt.

When diethylamine in the above reaction is replaced by an equimolar amount of the compounds of Table I, below, then the corresponding product is prepared.

EXAMPLE 16

N-isopropyl α-chloro-6-methoxy-2-naphthylacetamide

A mixture of 5 g. (0.016 moles) of ethyl α-chloro-6-methoxy-2-naphthylacetate and 5.5 ml. of anhydrous isopropylamine are stirred over Linde 4A molecular sieve for 16 hours at room temperature. The reaction mixture is filtered and excess isopropylamine is removed in vacuo. The residue is taken up in ether and washed three times with 15 ml. of 10% hydrochloric acid. The ether layer is dried over sodium sulfate, filtered, and the ether is removed. The residue is triturated with n-hexane and the precipitate is collected to obtain N-isopropyl α-chloro-6-methoxy-6-naphthylacetamide.

When isopropylamine in the above reaction is replaced by an equimolar amount of the compound of Table I, below, then the corresponding product is prepared.

Table I

| | |
|---|---|
| diethylamine | isothiazolidine |
| ethylmethylamine | piperidine |
| t-butylamine | morpholine |
| cyclopropylamine | N-methylpiperazine |
| N-methylhomopiperazine | |

When isopropylamine in the above reaction is replaced by ammonia, methylamine or dimethylamine and the reaction carried out in a bomb at 150°C, then the product is prepared is α-chloro-6-methoxy-2-naphthylacetamide, N-methyl-α-chloro-6-methoxy-2-naphthylacetamide or N,N-dimethyl-α-chloro-6-methoxy-2-naphthylacetamide.

When the dl, d or l α-chloroacetates of this invention are used in the above reaction, then the corresponding amide is prepared.

EXAMPLE 17

Ethyl α-bromo-6-methoxy-2-naphthylacetate

To 0.0476 moles of ethyl 6-methoxy-2-naphthylglycolate there is added slowly with stirring at 40°–50°C 23 g. (0.053 moles) of phosphorus pentabromide. The mixture is stirred at room temperature for 16 hours, then diluted with 70 ml. of petroleum ether, and poured into 125 ml. of ice-cold water. The organic phase is separated, washed with saturated aqueous sodium hydrogen carbonate solution, dried over anhydrous sodium sulfate, filtered and the solvent removed in vacuo to obtain ethyl α-bromo-6-methoxy-2-naphthylacetate.

When ethyl 6-methoxy-2-naphthylglycolate in the above procedure is replaced by d ethyl 6-methoxy-2-naphthylglycolate, l ethyl 6-methoxy-2-naphthylglycolate or N-isopropyl 6-methoxy-2-naphthylglycolamide, then the products prepared are d ethyl α-bromo-6-methoxy-2-naphthylglycolate, l ethyl α-bromo-6-methoxy-2-naphthylglycolate or N-isopropyl α-bromo-6-methoxy-2-naphthylglycolamide.

When the above procedure is followed using the various glycolates and glycolamides of this invention, then the corresponding α-bromoacetates and α-bromoacetamides are prepared.

EXAMPLE 18

When the α-bromoacetates of Example 17 are hydrolyzed according to the procedures of Examples 13–13, then the corresponding dl, d and l α-bromo-6-methoxy-2-naphthylacetic acid compounds and the various α-bromoacetic acids are prepared.

EXAMPLE 19

When the α-bromoacetic acid compounds are reacted according to the procedures of Examples 14–15, then the corresponding α-bromoacetic acid salts are prepared.

EXAMPLE 20

Ethyl α-fluoro-6-methoxy-2-naphthylacetate

A mixture of 0.33 moles of ethyl α-bromo-6-methoxy-2-naphthylacetate is vigorously stirred at 130°–140°C with 29 g. (0.5 moles) of potassium fluoride in 100 ml. of ethylene glycol for 12 hours. The reaction mixture is cooled and 400 ml. of water is added and the crude product separates. The aqueous glycol mixture is extracted with ether, the ether is then dried, evaporated to dryness and upon distillation results in ethyl α-fluoro-6-methoxy-2-naphthylacetate.

When ethyl α-bromo-6-methoxy-2-naphthylacetate in the above procedure is replaced by d ethyl α-bromo-6-methoxy-2-naphthylacetate, l ethyl α-bromo-6-methoxy-2-naphthylacetate or N-isopropyl α-bromo-6-methoxy-2-naphthylacetamide, then the products prepared are d ethyl α-fluoro-6-methoxy-2-naphthylacetate, l ethyl α-fluoro-6-methoxy-2-naphthylacetate or N-isopropyl α-fluoro-6-methoxy-2-naphthylacetamide.

When the above procedure is followed using the various α-bromoacetates and α-bromoacetamides of this invention, then the corresponding α-fluoroacetates and α-fluoroacetamides are prepared.

EXAMPLE 21

When the α-fluoroacetates of Example 20 are hydrolyzed according to the procedures of Examples 12–13, then the corresponding α-fluoro-6-methoxy-2-naphthylacetic acid compound and the various α-fluoroacetic acids are prepared.

EXAMPLE 22

When the α-fluoroacetic acid compounds are reacted according to the procedures of Examples 14–15, then the corresponding α-fluoroacetic acid salts are prepared.

EXAMPLE 23

Ethyl α-iodo-6-methoxy-2-naphthylacetate

A mixture of 0.1 moles of ethyl α-bromo-6-methoxy-2-naphthylacetate and 150 g. of sodium iodide in 1 liter of anhydrous acetone is refluxed for 4 hours. The reaction mixture is then evaporated to dryness and extracted with ether. The ether is then washed with water, dried and evaporated to dryness to obtain ethyl α-iodo-6-methoxy-2-naphthylacetate.

When ethyl α-bromo-6-methoxy-2-naphthylacetate in the above procedure is replaced by d ethyl α-bromo-6-methoxy-2-naphthylacetate, l ethyl α-bromo-6-methoxy-2-naphthylacetate or N-isopropyl α-bromo-6-methoxy-2-naphthylacetamide, then the products prepared are d ethyl α-iodo-6-methoxy-2-naphthylacetate, l ethyl α-iodo-6-methoxy-2-naphthylacetate or N-isopropyl α-iodo-6-methoxy-2-naphthylacetamide.

When the above procedure is followed using the various α-bromoacetates and α-bromoacetamides of this invention then the corresponding α-iodoacetates and α-iodoacetamides are prepared.

EXAMPLE 24

When the α-iodoacetates of Example 23 are hydrolyzed according to the procedures of Examples 12–13, then the corresponding α-iodo-6-methoxy-2-naphthylacetic acid compound and the various α-iodoacetic acids are prepared.

EXAMPLE 25

When the α-iodoacetic acid compounds are reacted according to the procedures of Examples 14–15, then the corresponding α-iodoacetic acid salts are prepared.

EXAMPLE 26

α-Mercapto-6-mehoxy-2-naphthylacetic acid

A mixture of 0.05 moles of α-chloro-6-methoxy-2-naphthylacetic acid and 5 g. of sodium hydrosulfide in 100 ml. of absolute ehtanol and under a nitrogen atmosphere is stirred for 15 hours. The mixture is then acidified with 6 N hydrochloric acid. The solvent is removed in vacuo and the residue is extracted into ether, washed with water, saturated sodium chloride solution, dried and evaporated to dryness to obtain α-mercapto-6-methoxy-2-naphthylacetic acid.

When the α-chloroacetates and α-chloroacetamides of this invention are used in the above reaction, then the corresponding α-mercaptoacetates and α-mercaptoacetamides are prepared.

EXAMPLE 27

α-Methylthio-6-methoxy-2-naphthylacetic acid

Methyl mercaptan is bubbled into a solution of 18.4 g. of potassium t-butoxide in 100 ml. of t-butanol for 3/4 hours and under a nitrogen atmosphere. To this is added 0.041 moles of α-chloro-6-methoxy-2-naphthylacetic acid in 60 ml of dry tetrahydrofuran. The mixture is then refluxed for 3 hours and allowed to stir at room temperature for 15 hours, acidified with 30 ml. of 6 N hydrochloric acid. The solvent is removed in vacuo and the residue extracted into ether, washed with water, saturated sodium chloride solution, dried and evaporated to dryness to obtain α-methylthio-6-methoxy-2-naphthylacetic acid.

When the α-chloroacetates and α-chloroacetamides of this invention are used in the above reaction, then the corresponding α-methylthioacetates and α-methylthioacetamides are prepared.

EXAMPLE 28

α-Acetylthio-6-methoxy-2-naphthylacetic acid

To a solution of 600 ml. of anhydrous ethanol and 21 g. (0.317 moles) of potassium hydroxide is added 45 ml. of thioacetic acid dropwise. To this mixture is then added 0.244 moles of α-chloro-6-methoxy-2-naphthylacetic acid and stirring is continued for 15 hours. The solid which forms is filtered off and washed with ethanol. The filtrate is evaporated to dryness and the residue is dissolved in 500 ml. of ether and washed several times with water. Drying the ether and evaporation to dryness results in α-acetylthio-6-methoxy-2-naphthylacetic acid.

In a similar manner, the α-propionylthio-6-methoxy-2-naphthylacetic acid compounds are prepared.

When the α-chloroacetates and α-chloroacetamides of this invention are used in the above reaction, then the corresponding α-acetylthioacetates and α-acetylthioacetamides are prepared.

EXAMPLE 29

α-Benzoylthio-6-methoxy-2-naphthylacetic acid

To 17.5 ml. of 2N alcoholic potassium hydroxide solution (0.035 mole) is added 4.84 g. (0.035 mole) of thiobenzoic acid. The solution is cooled to room temperature and to this is added in small portions 0.035 mole of α-chloro-6-methoxy-2-naphthylacetic acid. The reaction mixture is stirred at room temperature for 25 hours, then the solvent is removed, the residue dissolved in ether, filtered and washed with cold water. The ethereal solution is then dried over magnesium sulfate and evaporated to dryness to obtain α-benzoylthio-6-methoxy-2-naphthylacetic acid.

When the α-chloroacetates and α-chloroacetamides of this invention are used in the above reaction, then the corresponding α-benzoylthioacetates and α-benzoylthioacetamides are prepared.

EXAMPLE 30

Ethyl α-thioacetylthio-6-methoxy-2-naphthylacetate

A mixture of 0.2 moles of sodium dithioacetate and 0.12 moles of ethyl α-chloro-6-methoxy-2-naphthylacetate in 300 ml. of absolute ethanol is stirred at room temperature for 15 hours. The reaction mixture is filtered, washed with absolute ethanol and evaporated to dryness in vacuo. The residue is treated with ether, filtered and evaporated to dryness to obtain ethyl α-thioacetylthio-6-methoxy-2-naphthylacetate.

When the α-chloroacetates and α-chloroacetamides of this invention are used in the above reaction, then the corresponding α-thioacetylthioacetates and α-thioacetylthioacetamides are prepared.

When sodium dithioformate is used in the above procedure in place of sodium dithioacetate then the product prepared is ethyl α-thioformylthio-6-methoxy-2-naphthylacetate.

EXAMPLE 31

α-Thiocyanato-6-methoxy-2-naphthylacetic acid

To a solution of 300 ml. of anhydrous ethanol and 0.15 moles of sodium thiocyanate is added 0.12 moles of α-chloro-6-methoxy-2-naphthylacetic acid and stirred for 15 hours. The reaction mixture is filtered and washed with absolute ethanol. The filtrate is evaporated to dryness, the residue is dissolved in 250 ml. of ether and washed several times with water. The ether is then dried and evaporated to dryness to obtain α-thiocyanato-6-methoxy-2-naphthylacetic acid.

When the α-chloroacetate and α-chloroacetamides of this invention are used in the above reaction, then the corresponding α-thiocyanatoacetates and α-thiocyanatoacetamides are prepared

EXAMPLE 32

α-Sulfo-6-methoxy-2-naphthylacetic acid, disodium salt

To a solution of 250 ml. of anhydrous ethanol and 0.12 moles of sodium sulfite is added 0.1 moles α-chloro-6-methoxy-2-naphthylacetic acid, sodium salt. The reaction mixture is stirred for 15 hours, filtered and the residue worked with ethanol. The filtrate is evaporated to dryness to obtain α-sulfo-6-methoxy-2-naphthylacetic acid, disodium salt.

When sodium sulfinate is used in the above procedure in place of sodium sulfite, then the product obtained is α-sulfin-6-methoxy-2-naphthylacetic acid, disodium salt.

When the α-chloroacetates and α-chloroacetamides of this invention are used in the above reactions, then the corresponding α-sulfo and α-sulfinoacetates and amides are prepared.

EXAMPLE 33

Ethyl α-thiosulfo-6-methoxy-2-naphthylacetate, sodium salt

A mixture of 0.023 moles of ethyl α-chloro-6-methoxy-2-naphthylacetate and 5.7 g. of sodium thiosulfate pentahydrate in 75 ml. of 40:45 water-alcohol mixture is refluxed for 2 hours. An additional 0.8 g. of sodium thiosulfate pentahydrate is then added and refluxing continued another one-half hour. The reaction mixture is then evaporated to dryness in vacuo, azeotroped with ethanol and evaporated to dryness in vacuo again. The residue is triturated with ether, filtered and evaporated to dryness. The residue is then triturated with hexane and the resultant gum is dissolved in alcohol and evaporated to dryness in vacuo to obtain ethyl α-thiosulfo-6-methoxy-2-naphthylacetate, sodium salt.

When the α-chloroacetates and α-chloroacetamides of this invention are used in the above reaction, then the corresponding α-thiosulfoacetates and α-thiosulfoacetamides are prepared.

EXAMPLE 34

α-Amidinothio-6-methoxy-2-naphthylacetic acid, hydrochloride

Thiourea 15.2 g. (0.2 moles) is dissolved in 150 ml. of absolute ethanol and to this is added 0.11 moles of α-chloro-6-methoxy-2-naphthylacetic acid. The mixture is stirred for 15 hours at 0°C. The mixture is then filtered to obtain α-amidinothio-6-methoxy-2-naphthylacetic acid, hydrochloride.

When the α-chloroacetates and acetamides of this invention are used in the above procedures then the corresponding α-amidinoacetates and acetamides are prepared.

EXAMPLE 35

α-Ethoxythiocarbamylthio-6-methoxy-2-naphthylacetic acid

Ethylxanthic acid, potassium salt, 3.63 g. (0.22 moles) is dissolved in 150 ml. of absolute ethanol stirring. To this solution is added 0.11 moles of α-chloro-6-methoxy-2-naphthylacetic acid and the mixture stirred for 15 hours. The solid which collects is separated and washed with absolute ethanol. The solid is then treated with acetone and the insoluble material filtered off. The filtrate is concentrated to dryness to obtain α-ethoxythiocarbamylthio-6-methoxy-2-naphthylacetic acid.

When the α-chloroacetates and acetamides of this invention are used in the above procedure then the corresponding α-ethylxanthylacetates and acetamides are prepared.

EXAMPLE 36

α-Ethoxycarbonylthio-6-methoxy-2-naphthylacetic acid

A solution of α-mercapto-6-methoxy-2-naphthylacetic acid (0.02 moles) in 25 ml. of pyridine is cooled in an ice bath. To this is added dropwise 2.1 mol (0.022 moles) of ethyl chloroformate. The mixture is then stirred for 2 hours, diluted with ether and filtered. The mixture is basified with 10% sodium bicarbonate solution. The alkaline mixture is worked with ether, then acidified with 10% hydrochloric acid, washed with ether, dried and filtered. The solvent is removed and the residue is triturated with hexane to obtain α-ethoxycarbonylthio-6-methoxy-2-naphthylacetic acid.

When the α-mercaptoacetates and acetamides of this invention are used in the above procedure then the corresponding α-ethoxycarbonylthioacetates and acetamides are prepared.

EXAMPLE 37

α-Diethylcarbamylthio-6-methoxy-2-naphthylacetic acid

A solution of α-mercapto-6-methoxy-2-naphthylacetic acid (0.2 moles) in 25 ml. of pyridine is cooled in an ice bath. To this is added dropwise 0.022 moles of diethylcarbamylchloride. The mixture is then stirred for 2 hours, diluted with ether and filtered. The mixture is then basified with 10% sodium bicarbonate solution. The alkaline mixture is washed with ether, acidified with 10% hydrochloric acid, extracted with ether which in turn is washed with cold water, dried and evaporated to dryness. Trituration with hexane results in α-diethylcarbamylthio-6-methoxy-2-naphthylacetic acid.

When diethylcarbamylchloride is replaced in the above procedure by carbamyl chloride (prepared in situ from potassium cyanate and anhydrous hydrogen chloride in anhydrous chloroform), ethylcarbamyl chloride or dimethylcarbamyl chloride, then the products prepared are α-carbamylthio-6-methoxy-2-naphthylacetic acid, α-ethylcarbamylthio-6-methoxy-2-naphthylacetic acid or α-dimethylcarbamylthio-6-methoxy-2-naphthylacetic acid.

When the α-mercaptoacetates and acetamides of this invention are used in the above procedure then the corresponding α-carbamylthioacetates and acetamides are prepared.

EXAMPLE 38

When the procedure of Example 37 is followed but diethylcarbonate is replaced by succinic anhydride, maleic anhydride or phthalic anhydride, then the products prepared are α-hydrogen succinicthio-6-methoxy-2-naphthylacetic acid, α-hydrogen maleylthio-6-methoxy-2-naphthylacetic acid and α-(σ-carboxybenzoylthio)-6-methoxy-2-naphthylacetic acid.

When the various α-mercaptoacetates and acetamides of this invention are used in the above procedure, then the corresponding product is prepared.

EXAMPLE 39

When α-methylthio-6-methoxy-2-naphthylacetic acid is treated with 30% hydrogen peroxide, then the resultant product is α-methylsulfinyl-6-methoxy-2-naphthylacetic acid or α-methylsulfonyl-6-methoxy-2-naphthylacetic acid.

We claim:
1. A compound which is α-acetylthio-6-methoxy-2-naphthylacetic acid.
2. A compound which is α-propionylthio-6-methoxy-2-naphthylacetic acid.
3. A compound which is α-benzoylthio-6-methoxy-2-naphthylacetic acid.
4. A compound which is α-thioacetylthio-6-methoxy-2-naphthylacetic acid.
5. A compound which is α-thioformylthio-6-methoxy-2-naphthylacetic acid.

* * * * *